US012458617B2

(12) United States Patent
Jackson et al.

(10) Patent No.: US 12,458,617 B2
(45) Date of Patent: Nov. 4, 2025

(54) PET FOOD COMPOSITIONS COMPRISING CAPRYLIC ACID AND DOCOSAHEXAENOIC ACID AND/OR EICOSAPETAENOIC ACID FOR USE IN TREATING STRUVITE UROLITHIASIS

(71) Applicant: Hill's Pet Nutrition, Inc., Topeka, KS (US)

(72) Inventors: Matthew Jackson, Topeka, KS (US); Dennis Jewell, Lawrence, KS (US)

(73) Assignee: Hill's Pet Nutrition, Inc., Overland Park, KS (US)

( * ) Notice: Subject to any disclaimer, the term of this patent is extended or adjusted under 35 U.S.C. 154(b) by 1042 days.

(21) Appl. No.: 17/594,776

(22) PCT Filed: May 24, 2019

(86) PCT No.: PCT/US2019/033899
§ 371 (c)(1),
(2) Date: Oct. 29, 2021

(87) PCT Pub. No.: WO2020/242437
PCT Pub. Date: Dec. 3, 2020

(65) Prior Publication Data

US 2022/0202759 A1 Jun. 30, 2022

(51) Int. Cl.

| | |
|---|---|
| ***A61K 31/202*** | (2006.01) |
| ***A23K 20/158*** | (2016.01) |
| ***A23K 50/42*** | (2016.01) |
| ***A61K 9/00*** | (2006.01) |
| ***A61K 31/20*** | (2006.01) |

(52) U.S. Cl.
CPC .......... *A61K 31/202* (2013.01); *A23K 20/158* (2016.05); *A23K 50/42* (2016.05); *A61K 9/0056* (2013.01); *A61K 31/20* (2013.01)

(58) Field of Classification Search
CPC .... A61K 31/202; A61K 31/20; A23K 20/158; A23K 50/42; A23K 50/40
See application file for complete search history.

(56) References Cited

U.S. PATENT DOCUMENTS

| | | | |
|---|---|---|---|
| 7,776,375 | B2 | 8/2010 | Berthelot et al. |
| 8,032,436 | B2 | 10/2011 | Allderdice |
| 9,408,817 | B2 | 8/2016 | Khoo et al. |
| 9,789,079 | B2 | 10/2017 | Yuanlong et al. |
| 10,130,603 | B2 | 11/2018 | Jewell |
| 2004/0109881 | A1 | 6/2004 | Zdenek et al. |
| 2010/0292330 | A1 | 11/2010 | Larson et al. |

FOREIGN PATENT DOCUMENTS

| | | |
|---|---|---|
| JP | 2018-075042 | 5/2018 |
| WO | 2015/069215 | 5/2015 |

OTHER PUBLICATIONS

Sang et al: "Function of capric acid in cyclophosphamide-induced intestinal inflammation, oxidative stress, and barrier function in pigs", Scientific Reports, vol. 7, No. 1, 2017. (Year: 2017).*

(Continued)

*Primary Examiner* — Deborah D Carr

(57) ABSTRACT

Disclosed herein are pet food compositions for treating or preventing—inter alia—struvite urolithiasis comprising at N least one of caprylic acid and capric acid; and at least one of docosahexaenoic acid (DHA) and eicosapentaenoic acid (EPA).

18 Claims, 3 Drawing Sheets

(56) References Cited

OTHER PUBLICATIONS

Matsumoto et al., "Factors affecting struvite (MgNH4PO4.6H2O) crystallization in feline urine," Biochimica et Biophysica Acta, vol. 1780, 2008, p. 233-239.
Funaba et al., Faculty of Veterinary Medicine of Azabu University in City Sagamihara 229-8501 (English Translation), Journal of Pet Animal Nutrition, 2002, vol. 5, No. 1, p. 26-37.
Carlson et al., 2015, "The Additon of Medium-Chain Triglycerides to a Purified Fish Oil Based Diet Alters Inflammatory Profiles in Mice," Metabolism 64(2): 274-282.
International Search Report and the Written Opinion of the International Searching Authority issued in International Application PCT/US2019/033899 mailed Feb. 21, 2020.
Kono et al., 2010, "Enteral diets enriched with medium-chain triglycerides and N-3 fatty acids prevent chemically induced experimental colitis in rats," Translational Research 156(5):282-291.
Lee et al., 2017, "Function of Capric Acid in Cyclophosphamide-Induced Intestinal Inflammation, Oxidative Stress, and Barrier Function in Pigs," Scientific Reports 7(1):1-12.
Ortiz-Alvarado et al., 2012, "Omega-3 Fatty Acids Eicosapentaenoic Acid and Docosahexaenoic Acid in the Management of Hypercalciuric Stone Formers," Urology 79(2):282-286.

* cited by examiner

| Biochemical | Statistics | Invention | CTRL | MCT | FO |
|---|---|---|---|---|---|
| GG-FLN-GLY | Mean | -0.52 | -0.08 | -0.03 | 0.04 |
| | Std Err | 0.07 | 0.06 | 0.08 | 0.02 |
| FLN - GLY | Mean | -0.50 | -0.21 | -0.16 | -0.02 |
| | Std Err | 0.07 | 0.08 | 0.06 | 0.05 |
| FLN - GLY | Mean | -0.26 | -0.12 | 0.09 | 0.02 |
| | Std Err | 0.06 | 0.06 | 0.07 | 0.05 |

| Biochemical | Statistics | Invention | CTRL | MCT | FO |
|---|---|---|---|---|---|
| SAH | Mean | -0.76 | 0.13 | -0.14 | -0.15 |
| | Std Err | 0.16 | 0.15 | 0.13 | 0.13 |
| CYST | Mean | -0.44 | 0.02 | -0.22 | 0.07 |
| | Std Err | 0.09 | 0.06 | 0.06 | 0.05 |
| CYS | Mean | -0.17 | 0.08 | -0.08 | -0.10 |
| | Std Err | 0.05 | 0.03 | 0.06 | 0.06 |
| CYS - GLY | Mean | -0.45 | 0.03 | -0.32 | -0.28 |
| | Std Err | 0.05 | 0.11 | 0.12 | 0.07 |
| GSSG | Mean | -0.21 | 0.15 | -0.07 | 0.11 |
| | Std Err | 0.07 | 0.06 | 0.07 | 0.06 |
| CYSSG | Mean | -0.13 | 0.07 | -0.02 | 0.02 |
| | Std Err | 0.04 | 0.04 | 0.04 | 0.03 |
| OPH | Mean | 0.80 | 0.15 | 0.43 | -0.27 |
| | Std Err | 0.24 | 0.18 | 0.27 | 0.13 |
| pGLN | Mean | 0.55 | 0.03 | 0.10 | 0.04 |
| | Std Err | 0.07 | 0.07 | 0.10 | 0.05 |

PET FOOD COMPOSITIONS COMPRISING CAPRYLIC ACID AND DOCOSAHEXAENOIC ACID AND/OR EICOSAPETAENOIC ACID FOR USE IN TREATING STRUVITE UROLITHIASIS

BACKGROUND

Inflammation and its associated proinflammatory substances are part of an animal's immunological response to such challenges as disease or invading pathogens. Inflammation, which can be internal, external or both, sometimes occurs persistently and at levels that negatively impact the health of the animal. At times, the sustained and/or elevated production of proinflammatory substances such as cytokines may cause inflammation to work against the body's tissues and cause damage.

Inflammation can be classified as either acute or chronic. Acute inflammation is an initial response to harmful stimuli and is achieved by the increased movement of plasma and leukocytes from the blood into the injured tissues. A cascade of biochemical events propagates and matures the inflammatory response, involving the local vasculature, the immune system, and various cells within the injured tissue. Chronic inflammation, or prolonged inflammation, leads to a progressive shift in the type of cells that are present at the site of inflammation and is characterized by simultaneous destruction and healing of the tissue from the inflammatory process.

One inflammatory disorder, for example, is inflammatory bowel disease. The terms "inflammatory bowel disease" or "IBD" refer to a group of chronic idiopathic gastrointestinal disorders characterized by inflammatory infiltrates within the lamina propia of the gastrointestinal tract. IBD encompasses disorders such as segmental granulomatous enterocolitis, lymphoplasmacytic enteritis, eosinophilic gastroenterocolitis, lymphocytic gastroenterocolitis, suppurative enterocolitis, and histiocytic colitis. The specific types of IBD are characterized based on the type of inflammatory infiltrate found in the lamina propia. The inflammatory infiltrates can be quite variable in terms of severity and cell types, with lymphocytes and plasma cells being the most common cell types. Inflammatory infiltrates may involve the stomach, small bowel, and colon. In cats, for example, the stomach and small bowel are affected most often. In many cases, multiple segments of the bowel are involved and clinical signs may be mixed, reflecting the broad distribution of mucosal lesions. The severity of IBD varies from mild clinical signs to life-threatening protein-losing enteropathies.

Mucosal inflammation disrupts normal absorptive processes. Such disruption results in malabsorption and osmotic diarrhea. Altered gut permeability can result in leakage of fluid, protein, and blood into the gut lumen. Malabsorbed fats, carbohydrates, and bile acids result in secretory diarrhea. Inflammation of the stomach and small bowel stimulates receptors that trigger vomiting. In cats, for example, the most common clinical signs of IBD are chronic vomiting, diarrhea, and weight loss.

Certain inflammatory responses involving the gastrointestinal tract can occur as a result of dysbiosis, or the imbalance of resident microorganisms. In a series of events involving several aspects of host immune response, bacterial toxins such as lipopolysaccharides (LPS) may stimulate defense processes that include production of proinflammatory substances, such as cytokines, prostanoids, proteases and/or reactive oxygen species. These substances have a function in defense against microbial invaders, but they can also cause collateral tissue damage and contribute to the load of substances associated with inflammatory processes and tissue destruction systemically. Accordingly, an animal's cytokine level may be indicative of the its present inflammatory state, and management and/or reduction of proinflammatory substances such as cytokines in an animal may be beneficial to that animal's health.

Despite ongoing research aimed at understanding inflammation and the role proinflammatory substances play in tissue damage or disease progression, effective management of inflammatory conditions has remained a challenge. Although a number of conventional treatments exist, such treatments have drawbacks including side effects, and may actually be harmful or make the condition worse. For example, steroids can fight inflammation by reducing the production of inflammatory chemicals and are often prescribed for conditions including asthma, inflammatory bowel disease, and inflammatory arthritis. But steroids can have considerable side-effects and are one of the most frequently abused drugs in veterinary and human medicine. There remains, therefore, a need for new or alternative methods and compositions for treating or preventing an inflammatory condition.

As discussed above, inflammation may be a result of dybiosis. An animal's microbiome, which comprises the bacteria and microorganisms resident in the animal's gastrointestinal tract, affects the animal's health. Dysbiosis is a reduction in the proportion of beneficial bacteria and an increase in deleterious bacteria in the gastrointestinal tract. This bacterial imbalance can cause the accumulation of toxic microbial metabolites in the animal's body, which may lead to inflammation, as well as oxidative stress and other various diseases. Accordingly, decreasing the levels of various postbiotics, or metabolic derivatives produced from deleterious bacteria, in an animal's microbiome may be beneficial to the health of the animal. Postbiotics may include, for example, microbiome-derived indole derivatives, sulfated hologenomic metabolites, and phenolic derivatives.

In addition to inflammatory and altered microbiomic conditions, there also exist health concerns for an animal surrounding aging of the animal, including, for example, the aging animal's decreased ability to metabolize fat. Carnitine is a compound involved in the metabolism of fat by the oxidation of fatty acids, and therefore carnitine and its metabolite N-Acetyl L-Carnitine (ALCAR) are believed to be useful in the treatment or prevention of age-related health concerns in companion animals. Accordingly, an animal's carnitine and ALCAR derivative levels may be indicative of the its ability to metabolize fat, and management and/or reduction of other age-related concerns. There remains, therefore, a need for new or alternative methods and compositions for increasing an animal's carnitine and ALCAR derivative levels.

BRIEF SUMMARY

Disclosed herein are pet food compositions for treating or preventing inflammation or an inflammatory disorder in a companion animal comprising an effective amount of at least one medium chain triglyceride (MCT) and an effective amount of at least one omega-3 fatty acid, wherein the amount of the at least one MCT and the at least one omega-3 fatty acid provides a synergistic decrease in the amount of circulating cytokines in the companion animal after the companion animal consumes the pet food composition.

In certain embodiments, disclosed herein are pet food compositions for treating or preventing inflammation or an inflammatory disorder in a companion animal comprising an effective amount of at least one of caprylic acid and capric acid present in an amount of at least about 1%, such as ranging from about 1% to about 7%, by weight based on the total weight of the pet food composition, and an effective amount of at least one of docosahexaenoic acid (DHA) and eicosapentaenoic acid (EPA) present in an amount of at least about 0.2%, such as ranging from about 0.2% to about 3%, by weight based on the total weight of the pet food composition, wherein the amount of the at least one of caprylic acid and capric acid and the at least one of DHA and EPA provides a synergistic decrease in the amount of circulating cytokines in the companion animal after the companion animal consumes the pet food composition.

In certain embodiments disclosed herein, the effective amount of the at least one of caprylic acid and capric acid is about 7% by weight based on the total weight of the pet food composition. In certain embodiments, the effective amount of the at least one of DHA and EPA ranges from about 2% to about 3% by weight based on the total weight of the pet food composition, and in certain embodiments, the ratio of DHA to EPA in the pet food composition is at least about 7:1. In certain embodiments, the companion animal is a cat.

According to various embodiments of the disclosure, the at least one of caprylic acid and capric acid may be added to the pet food composition in the form of an oil chosen from coconut oil, palm oil, and palm kernel oil, and according to certain embodiments, the at least one of DHA and EPA may be added to the pet food composition in the form of fish oil.

Further disclosed herein are methods for treating or preventing inflammation in a companion animal in need thereof comprising administering to the companion animal a pet food composition comprising an effective amount of at least one of caprylic acid and capric acid and an effective amount of at least one of DHA and EPA, wherein the administration of the composition results in a synergistic decrease in the amount of cytokines in the companion animal. In certain embodiments, the companion animal is a cat.

According to certain embodiments of the methods for treating or preventing inflammation disclosed herein, the inflammation is chronic inflammation, and in certain embodiments, the inflammation is acute inflammation.

In certain embodiments of the methods disclosed herein, the effective amount of the at least one of caprylic acid and capric acid is at least about 1.1%, such as ranging from about 1.1% to about 7%, based on the total weight of the pet food composition, and in certain embodiments, the effective amount of the at least one of DHA and EPA is at least about 0.2%, such as ranging from about 0.2% to about 3%, based on the total weight of the pet food composition.

In another embodiment of the methods disclosed herein, the cytokines are chosen from at least one of Fas, GM-CSF, IL-2, IL-13, IL-8, and SDF-1, and according to certain embodiments, the inflammation is chronic inflammation. According to other embodiments of the disclosure, the cytokines are chosen from at least one of Fas, GM-CSF, IL-2, IL-13, SDF-1, and TNF-α, and in certain embodiments, the inflammation is acute inflammation.

In various embodiments of the methods disclosed herein, the administration of the pet food composition results in a synergistic increase in the amount of at least one of camitine and N-Acetyl L-Carnitine in the companion animal. Furthermore, in various embodiments of the methods disclosed herein, the administration of the pet food composition results in a synergistic decrease in the amount of at least one postbiotic chosen from indoles, hologenomic sulfates, and phenolics in the companion animal.

Further areas of applicability of the present disclosure will become apparent from the detailed description provided hereinafter. It should be understood that the detailed description and specific examples, while indicating the preferred embodiments of the disclosure, are intended for purposes of illustration only and are not intended to limit the scope of the disclosure.

DETAILED DESCRIPTION

Figure 1:
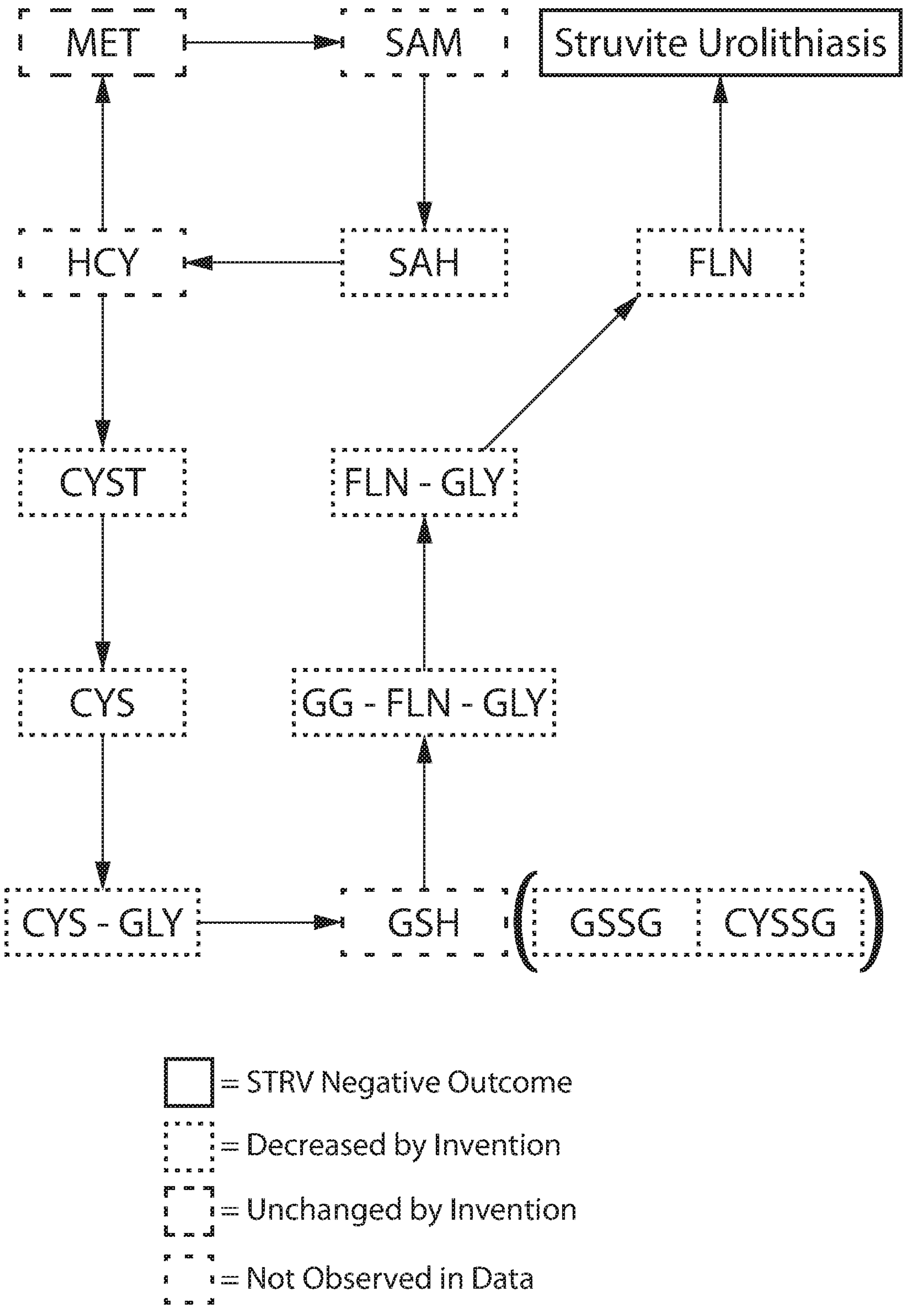
FIG. 1 is a flowchart depicting the impact of an amino acid on struvite urolithiasis risk in a companion animal.
Figure 2:
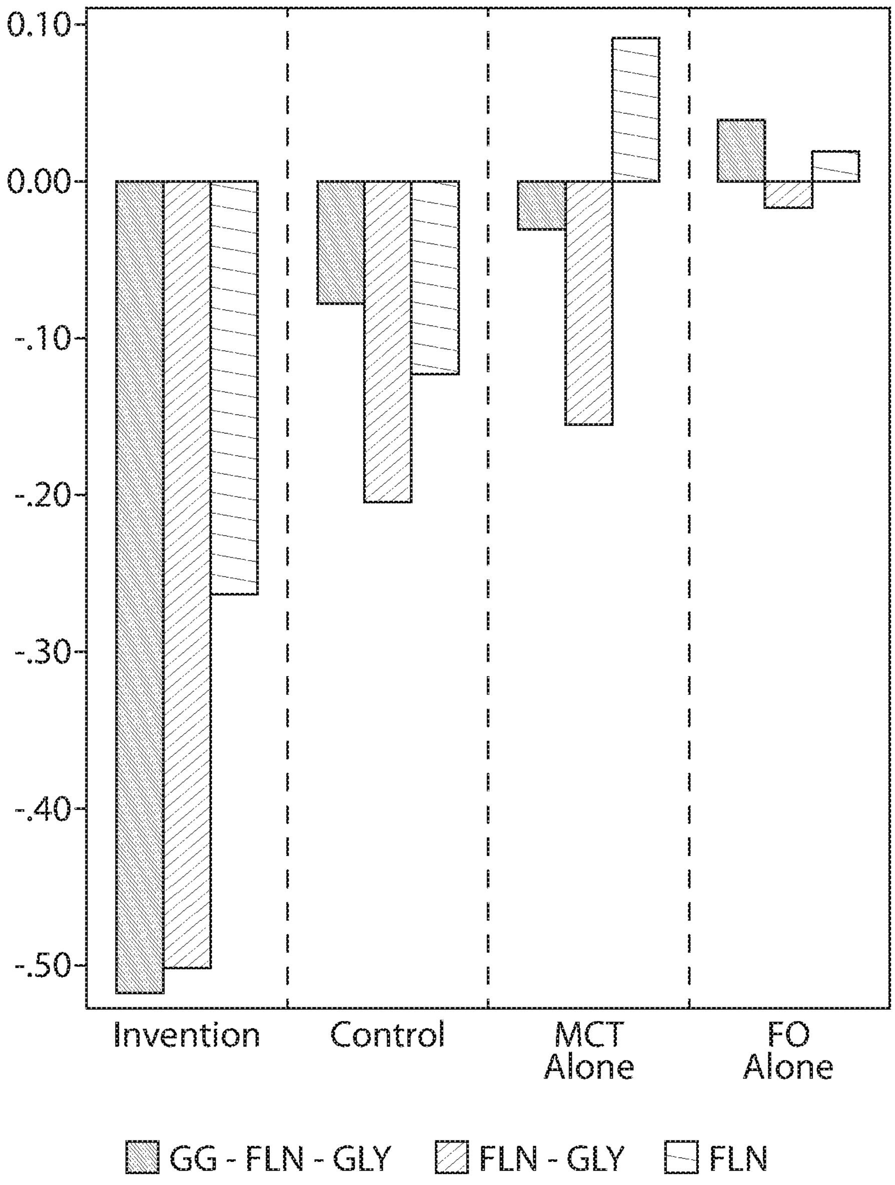
FIG. 2 depicts the impact that compositions of the present invention have on felinine, and precursors thereof.
Figure 3:
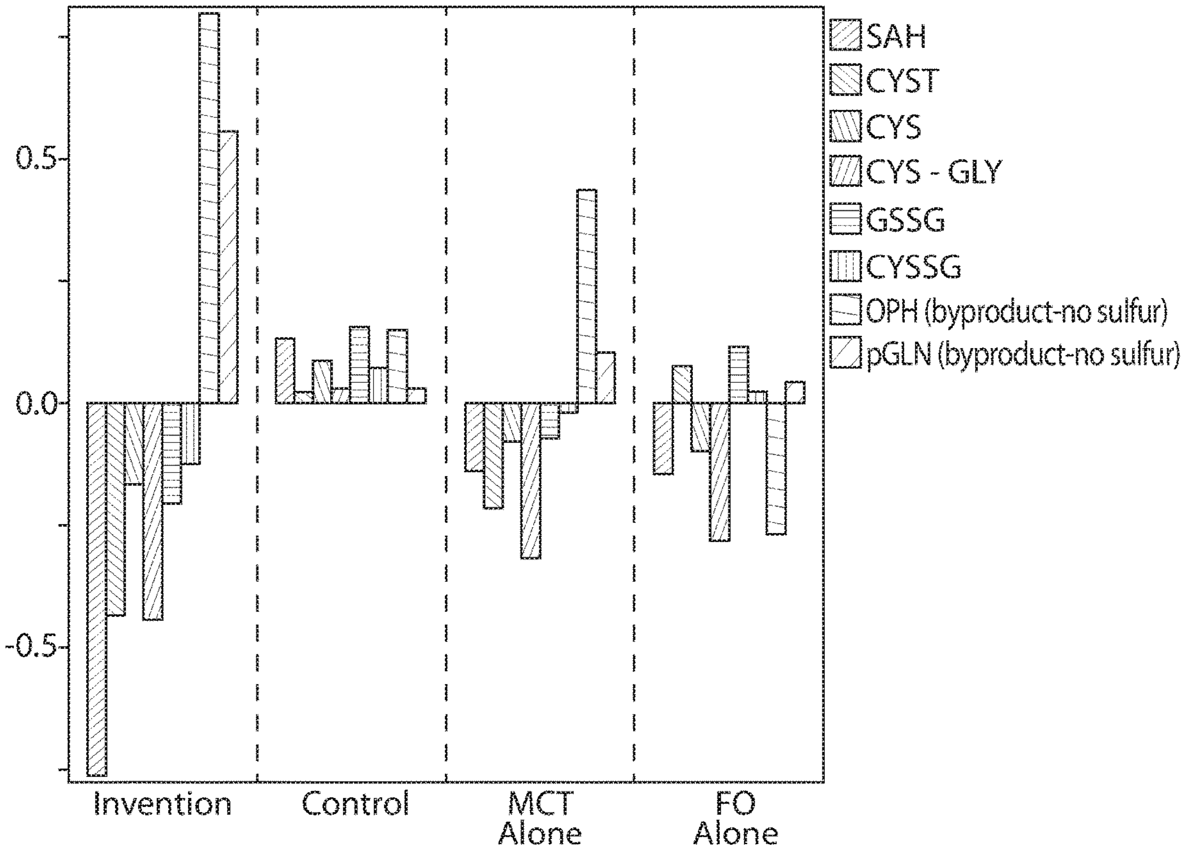
FIG. 3 depicts the impact that compositions of the present invention have on sulfur-containing amino acids and sulfur-free byproducts.

The following description of the preferred embodiments is merely exemplary in nature and is in no way intended to limit the invention, its application, or uses.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of"in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material. Unless otherwise specified, all component or composition amounts are in reference to the active amount of that component or composition, and exclude impurities or by-products, which may be present in commercially available sources.

All references cited herein are hereby incorporated by reference in their entireties. In the event of a conflict in a definition in the present disclosure and that of a cited reference, the present disclosure controls.

Disclosed herein are pet food compositions comprising at least one MCT and at least one omega-3 fatty acid in an amount effective to provide a synergistic decrease in the amount of circulating cytokines in the companion animal, such as in the blood of the companion animal. Also disclosed herein are methods to prevent or treat inflammation or an inflammatory disorder in a companion animal comprising administering an effective amount of at least one MCT and an effective amount of at least one omega-3 fatty acid, wherein the amount of the at least one MCT and the at least one omega-3 fatty acid is sufficient to synergistically decrease the amount of circulating cytokines in the companion animal, such as in the blood of the companion animal. Further disclosed herein are methods for reducing levels of cytokines generated upon stimulation by lipopolysaccharide (LPS), thereby reducing inflammation that may stem, for example, from dysbiosis of the gut bacteria microbiome.

The term "inflammatory disorder" herein not only refers to an inflammatory condition, disorder, or disease per se, but also to any condition, disorder, or disease that develops or progresses as a result of an inflammatory disorder. Illustratively, inflammatory disorders include, without limitation, gingivitis, periodontitis, rheumatoid arthritis, bursitis, osteoarthritis, systemic lupus, asthma, hepatitis, bronchitis, acute gouty arthritis, psoriatic arthritis, colitis, Crohn's disease, an allergic condition (e.g., bronchial asthma, allergic rhinitis, drug-induced dermatitis, contact and atopic dermatitis), a chronic skin condition (e.g., dermatitis herpetiformis, pemphigus, severe psoriasis and severe seborrheic dermatitis, chronic allergic and inflammatory conditions of the uvea, iris, conjunctiva and optic nerves of the eyes, an acute coronary syndrome (e.g., unstable angina, acute myocardial infarction, sudden cardiac death, coronary plaque rupture, thrombosis), inflammatory bowel disease, and combinations thereof.

An inflammatory disorder can be acute or chronic. An inflammatory disorder, particularly a chronic condition, also can contribute to or be a risk factor for the development or progression of other conditions, disorders, or diseases, including, without limitation, cancer, cachexia, cardiovascular disease, diabetes, osteoporosis, and neurodegenerative disorders such as Alzheimer's disease.

Proinflammatory substances are signaling molecules, such as cytokines, that are known to enhance an inflammatory response in animals, such as, for example, fever, inflammation, and tissue destruction. A variety of proinflammatory substances are known to those skilled in the art. The level of proinflammatory substances in an animal may be increased by proinflammatory stimuli, such as LPS. LPS is located in the membrane of gram-negative bacteria and is known to trigger an immune response in an animal. As part of this immune response, LPS may trigger the production of various proinflammatory substances.

Proinflammatory substances may include, without limitation, eicosanoids such as, for example, prostaglandins (e.g., $PGE_2$) and leukotrienes (e.g., $LTB_4$); gases (e.g., nitric oxide (NO)); enzymes (e.g., phospholipases, inducible nitric oxide synthase (iNOS), COX-1 and COX-2); and cytokines such as, for example, interleukins (e.g., IL-1α, IL-1β, IL-2, IL-3, IL-4, IL-5, IL-6, IL-8, IL-10, IL-12, IL-13 and IL-18), members of the tumor necrosis factor family (e.g., TNF-α, TNF-β and lymphotoxin β), interferons (e.g., IFN-β and IFN-γ), granulocyte/macrophage colony-stimulating factor (GM-CSF), transforming growth factors (e.g., TGF-β1, TGF-β2 and TGF-β3, leukemia inhibitory factor (LIF), Fas ligand (Fas), stromal cell-derived factor 1 (SDF-1), ciliary neurotrophic factor (CNTF), migration inhibitory factor (MIF), monocyte chemoattractant protein (MCP-1), macrophage inflammatory proteins (e.g., MIP-1α, MIP-1β and MIP-2), and RANTES. In one embodiment, the proinflammatory substance is a cytokine. In another embodiment, the proinflammatory substance is selected from the group consisting of Fas, GM-CSF, IL-2, IL-13, IL-8, SDF-1, and TNF-α.

In addition to synergistically decreasing the level of circulating cytokines in an animal, the pet food compositions disclosed herein may have further effects on circulating metabolites in the animal. For example, in certain embodiments, the pet food compositions disclosed herein may synergistically increase the levels of circulating carnitine and its blood brain barrier permeable metabolite ALCAR and/or may synergistically decrease the level of various postbiotics, such as for example, indole derivatives, sulfated hologenomic metabolites; and phenolic derivatives.

Accordingly, further disclosed herein are pet food compositions comprising at least one MCT and at least one omega-3 fatty acid that are effective to synergistically increase the levels of circulating carnitine and/or ALCAR derivative levels in companion animals who consume the pet food composition. Without being bound by theory, it is believed that this increase in circulating camitine and/or ALCAR derivative levels results in benefits to various aging conditions, where fat metabolism is often decreased relative to a youthful state. Also disclosed herein are methods of treating or preventing age-related disorders by administering a pet food composition to a companion animal in need thereof comprising at least one MCT and at least one omega-3 fatty acid, wherein the pet food composition synergistically increases circulating carnitine derivative levels and/or ALCAR derivative levels of the companion animal, with a resultant beneficial effect on global carnitine metabolism.

Exemplary non-limiting camitine and ALCAR derivatives may include docosahexanoylcarnitine, docosapentanoylcartinine, decanoylcaritine, dihomolinolenoylcarnitine, octadecenedioylcarnitine, butyrylcarnitine, laurylcamitine, nervonoylcarnitine, 5-dodecenoylcarnitine, myristoyleoylcarnitine, margaroylcarnitine, merotoylcarnitine, arachidonoylcarnitine, palmitoleoylcarnitine, linolenoylcarnitine, succinylcarnitine, deoxycarnitine, octonoylcarnitine, cis-4-decenoylcarnitine, benzoylcarnitine, lignoceroylcarnitine, adipoylcarnitine, carnitine, dihomo-linoleoylcarnitine, myristoylcamitine, propionylcarnitine, adrenoylcarnitine, octadecanedioylcarnitine, behenoylcarnitine, glutaroylcarnitine, arachidoylcarnitine, linoleoylcarnitine, stearoylcarnitine, palmitoylcarnitine, pimeloylcarnitine/3-methyladipoylcarnitine, phenylacetylcarnitine, eicosenoylcarnitine, oleoylcarnitine, suberoylcarnitine, hexanoylcarnitine, tiglyl carnitine, isobutyrylcarnitine, 3-hydroxtbutyrylcarnitine, isovalerylcarnitine, acetylcarnitine, 2-methylbutyroylcamitine, and erucoylcarnitine.

Also disclosed herein are pet food compositions for treating or preventing various renal, gastrointestinal, and dermatological conditions wherein the pet food composition comprises at least one MCT and at least one omega-3 fatty acid that may act as a microbiome dimmer switch to synergistically decrease postbiotic production of various metabolites, such as circulating microbiome-derived indole derivatives, circulating host and microbiome-derived sulfated hologenomic metabolites, and circulating microbiome-derived phenolic derivatives. Further disclosed herein are methods of treating or preventing various renal, gastrointestinal, and dermatological conditions comprising administering a pet food composition to a companion animal in need thereof comprising at least one MCT and at least one omega-3 fatty acid, wherein the pet food composition synergistically reduces levels of circulating microbiome-derived indole derivatives, circulating host and microbiome-derived sulfated hologenomic metabolites, and circulating microbiome-derived phenolic derivatives.

Exemplary non-limiting microbiome-derived indole derivatives may include 2-oxindole-3-acetate T-28-2-oxindole-3-acetate P-14; 3-hydroxyindolin-2-one sulfate T-28-3-hydroxyindole-2-one sulfate P-14; 5-hydroxyindole sulfate T-28-5-hydroxyindole sulfate P-14; 6-hydroxyindole sulfate T-28-6-hydroxyindole sulfate P-14; 7-hydroxyindole sulfate T-28-7-hydroxyindole sulfate P-14; indole-3-carboxylic acid T-28-indole-3-carboxylic acid P-14; indoleacetate T-28-indoleacetate P-14; indoleacetylglutamine T-28-indoleacetylglutamine P-14; indoleacetylglglycine T-28-indoleacetylglycine P-14; indoleacrylate T-28-indoleacrylate P-14; indoleacetate T-28-indoleacetate P-14; indolepropionate T-28-indolepropionate P-14; and indole-2-one T-28-indole-2-one P-14.

Exemplary non-limiting host and microbiome-derived sulfated hologenomic metabolites may include 2-aminophenol sulfate T-28-2-aminophenol sulfate P-14; 3-(3-hydroxyphenol)propionate sulfate T-28-3-(3-hydroxyphenol)propionate sulfate P-14; 4-acetylphenyl sulfate T-28-4-acetylphenyl sulfate P-14; 3-methoxycatechol sulfate (2) T-28-3-methoxycatechol sulfate (2) P-14; 4-ethylphenyl sulfate T-28-4-ethylphenyl sulfate P-14; 4-hydroxycinnamate sulfate T-28-4-hydroxycinnamate sulfate P-14; 4-methylcatechol sulfate T-28-4-methylcatechol sulfate P-14; 4-vinylguaiacol sulfate T-28-4-vinylguaiacol sulfate P-14; 4-vinylphenol sulfate T-28-4-vinylphenol sulfate P-14; hydroquinone sulfate T-28-hydroquinone sulfate P-14; isoeugenol sulfate T-28-isoeugenol sulfate P-14; equol sulfate T-28-equol sulfate P-14; and o-methylcatechol sulfate T-28-O-methylcatechol sulfate P-14.

Exemplary non-limiting microbiome-derived phenolic derivatives may include 2-hydroxyphenylacetate T-28-2-hydroxyphenylacetate P-14; 3-(3-hydroxyphenyl)propionate T-28-3-(3-hydroxyphenyl)propionate P-14; 3-(4-hydroxyphenyl)lactate (HPLA) T-28-3-(4-hydroxyphenyl) lactate (HPLA) P-14; 3-(4-hydroxyphenyl)propionate T-28-3-(4-hydroxyphenyl)propionate P-14; 3-hydroxy-3-phenylpropionate T-28-3-hydroxy-3-phenylpropionate P-14; 3-phenylpropionate (hydrocinnamate) T-28-3-phenylpropionate (hydrocinnamate) P-14; 4-hydroxyphenylacetylglycine T-28-4-hydroxyphenylacetylglycine P-14; 4-hydroxyphenylpryuvate T-28-4-hydroxyphenylpryuvate P-14; phenylacetate T-28-phenylacetate P-14; phenylacetylalanine T-28-phenylacetylalanine P-14, phenylacetylcamitine T-28-phenylacetylcarnitine P-14; phenylacetylglutamate T-28-phenylacetylglutamate P-14; phenylacetylglutamine T-28-phenylacetylglutamine P-14; phenylacetylglycine T-28-phenylacetylglycine P-14; phenylacetylserine T-28-phenylacetylserine P-14; phenyllactate (PLA) T-28-phenyllactate P-14; phenylpropionylglycine T-28-phenylpropionylglycine P-14; and phenylpyruvate T-28-phenylpyruvate P-14.

As used herein, the phrase “synergistic increase” in a level of a substance or substances refers to an increase in the level that is greater than the additive effect that would be expected from the combination of two or more agents, in view of the effect demonstrated by the agents on the level of the substance or substances independently. In some embodiments, a synergistic increase may be manifested, for example, by a lower amount of the agent or agents being needed to affect the desired result, and/or by a faster rate of achieving the desired result.

As used herein, the phrase “synergistic decrease” in level of a substance or substances refers to a decrease in the level that is greater than the additive effect that would be expected from the combination of two or more agents, in view of the effect demonstrated by the agents on the level of the substance or substances independently. In some embodiments, a synergistic decrease may be manifested, for example, by a lower amount of the agent or agents being needed to affect the desired result and/or by a faster rate of achieving the desired result.

As used herein, the term “medium chain triglyceride” (MCT) indicates a glycerol molecule ester-linked to three fatty acid molecules, each fatty acid molecule having 6-12 carbons. Any source of MCTs may be used in the pet food compositions according to the embodiments disclosed herein. Exemplary MCTs include, for example, caproic acid, caprylic acid, capric acid, or lauric acid.

Sources of MCTs include, for example, coconut oil, palm oil, and palm kernel oil. Coconut oil is an oil extracted from the kernel or meat of matured coconuts. Palm kernel oil is derived from the kernel of the oil palm, and palm oil is derived from the oil palm fruit itself. Coconut oil, palm oil, and palm kernel oil all comprise a high content of saturated fat. Because of their high saturated fat content, coconut oil, palm oil, and palm kernel oil may be used as a supplement in food and in medicine, as well as having other industrial applications. The MCTs disclosed herein may be prepared by any process known in the art. In certain embodiments disclosed herein, the MCT may be chosen from at least one of caprylic acid and caproic acid, and in certain embodiments the source of the MCT may be coconut and/or palm kernel oil. In certain embodiments the MCT is manufactured by the esterification of glycerin and fatty acids that originate from at least one of coconut oil and palm kernel oil, such as Captex@ 355 MCT. In certain embodiments, the source of the MCT, such as Captex@ 355 MCT, may comprise a distribution of various fatty acids, such as a distribution of caproic acid, caprylic acid, capric acid, and lauric acid. In certain embodiments, the distribution is such that the caprylic acid comprises about 50% to about 75% of the total distribution of fatty acids in the source of the MCT, and the capric acid comprises about 20 to about 45% of the total distribution of fatty acids in the source of the MCT.

As used herein, the term "omega-3 fatty acids" means a member of a group of polyunsaturated fatty carboxylic acids. In general, the omega-3 fatty acids contain 12-26 carbon atoms with methylene-interrupted double bonds, one of which is between the $3^{rd}$ and $4^{th}$ carbon atoms as counted from the methyl end of the fatty acid molecule. The physiologically more important omega-3 fatty acids are 18-22 carbons in length and straight chained. Illustratively, omega-3 fatty acids include, without limitation, EPA, DHA, alpha-linolenic acid (ALA), and derivatives thereof. In certain embodiments, omega-3 fatty acids may be included in food compositions as components of triglycerides. Additional non-limiting examples of derivatives include salts and esters, such as branched or unbranched and/or saturated or unsaturated $C_1$-$C_{30}$ alkyl and cycloalkyl esters of omega-3 fatty acids.

Any source of source of omega-3 fatty acids may be used according to the compositions and methods disclosed herein. For example, sources of omega-3 fatty acids include, without limitation, fish (e.g., menhaden, sardine, herring, tuna, salmon), fish oil, fish meal, plant oil, algae, algae oil, flax seed, flax seed oil, canola, canola oil, soybean, soybean oil, walnut, walnut oil, and mixtures thereof. As used herein, the term "fish oil" indicates a fatty or oily extract, relatively rich in omega-3 fatty acid. Fish oil may be either crude or purified and may be obtained from a variety of fish, such as, but not limited to, salmon, tuna, mackerel, herring, sea bass, striped bass, halibut, catfish, sardines and combination thereof.

An omega-3 fatty acid also can be obtained by chemical synthesis. An omega-3 fatty acid can be incorporated into preparations in the form of the free acid or as a pharmaceutically or nutritionally acceptable salt. The at least one omega-3 fatty acid can be in a highly purified, substantially purified, partially purified, or non-purified form. In one embodiment, the at least one omega-3 fatty acid is selected from the group consisting of EPA, DHA, and combinations thereof. In certain embodiments disclosed herein, the omega-3 fatty acid comprises a mixture of DHA and EPA. In certain embodiments, the source of the mixture of DPA and EPA is fish oil, and in certain embodiments, the mixture of DPA and EPA has a ratio of DPA to EPA of at least about 7:1.

The dosages of the at least one MCT and the at least one omega-3 fatty acid can be adjusted on a body weight basis and may thus be adapted to be suitable for any animal regardless of its size.

In one embodiment, the at least one MCT is present in the pet food composition in an amount of at least about 1.1%, such as at least about 2%, at least about 5%, at least about 7%, or about 7% by weight based on the total weight of the pet food composition. In certain embodiments, the at least one MCT is present in the pet food composition in an amount of less than about 7%, such as less than about 5% or less than about 2% by weight based on the total weight of the pet food composition. In certain embodiments, the at least one MCT is present in the pet food composition in an amount ranging from about 1.1% to about 7%, such as from about 2% to about 5%, by weight based on the total weight of the pet food composition.

In one embodiment, the at least one omega-3 fatty acid is present in the pet food composition in an amount of at least about 0.2%, such as at least about 0.5%, at least about 1%, at least about 1.5%, at least about 2%, at least about 2.5%, or at least about 3%, by weight based on the total weight of the pet food composition. In certain embodiments, the at least one omega-3 fatty acid is present in the pet food composition in an amount of less than about 3%, such as less than about 2%, or less than about 1.5% by weight based on the total weight of the pet food composition. In certain embodiments, the at least one omega-3 fatty acid is present in the pet food composition in an amount ranging from about 0.2% to about 3%, such as from about 1% to about 3%, or from about 1.5% to about 2.5%, by weight based on the total weight of the pet food composition.

In certain embodiments, the at least one MCT is present in about amount ranging from about 1.1% to about 7%, such as from about 2% to about 5%, or from about 5% to about 15%, by weight based on the total weight of the pet food composition, and the at least one omega-3 fatty acid is present in an amount ranging from about 0.2% to about 5%, such as about 1% to about 2.5%, or about 2% to about 3%, by weight based on the total weight of the pet food composition. In certain embodiments, the at least one MCT is present in an amount of at least about 1.1%, such as at least about 2%, at least about 5% or at least about 7%, by weight based on the total weight of the pet food composition, and the omega-3 fatty acid is present in an amount of at least about 0.2%, such as at least about 0.5%, at least about 1%, at least about 1.5%, at least about 2%, at least about 2.5%, or at least about 3%, by weight based on the total weight of the pet food composition. In one embodiment, the at least one MCT is present in an amount of about 7% and the at least one omega-3 fatty acid is present in an amount ranging from about 2% to about 3%, by weight based on the total weight of the pet food composition.

The pet food compositions disclosed herein may meet all of an animal's ordinary nutritional requirements, which a skilled artisan can determine based upon the animal's species, age, sex, weight, and other factors. In some embodiments, the pet food compositions disclosed herein provide a substantially nutritionally complete food for the intended recipient animal. A "nutritionally complete food" is a food that includes sufficient nutrients for maintenance of normal health of a healthy animal if the food provides substantially all of the animal's diet.

In certain embodiments, the pet food compositions disclosed herein may further comprise at least one protein source. Suitable protein sources may be selected from any suitable animal or vegetable source. For example, suitable protein sources may include at least one of poultry meal, poultry by-product meal, chicken meal, chicken by-product meal, lamb meal, meat and meat bone, fish meal, soy bean meal, soy protein concentrates, milk proteins, corn gluten meal, wheat gluten, and gluten. The starch source may also be a source of protein.

In certain embodiments, the pet food compositions disclosed herein may further comprise at least one fiber source. Fiber sources may, for example, be chosen from at least one vegetable fiber source, such as cellulose, beet pulp, peanut hulls, and soy fiber.

In certain embodiments the pet food compositions disclosed herein further comprise nutritional balancing agents. Nutritional balancing agents may be obtained from a variety of sources known to skilled artisans, for example, vitamin and mineral supplements and food ingredients. Vitamins and minerals can be included in amounts required to avoid deficiencies and maintain health. These amounts are readily available in the art. The American Feed Control Officials (AAFCO) provides recommended amounts of such nutrients for dogs and cats. Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the pet food compositions disclosed herein may comprise additional ingredients such as fillers, palatability enhancers, binding agents, flavors, stabilizers, emulsifiers, sweeteners, colorants, buffers, salts, coatings, and the like. Stabilizers include substances that tend to increase the shelf life of the compositions such as preservatives, synergists and sequestrants, packaging gases, emulsifiers, thickeners, gelling agents, and humectants. Examples of emulsifiers and/or thickening agents include gelatin, cellulose ethers, starch, starch esters, starch ethers, and modified starches. Specific amounts for each composition component will depend on a variety of factors such as the particular components included in the composition; the species of the animal; the animal's age, body weight, general health, gender, and diet; the animal's consumption rate; the type of disease or condition being treated, and the like.

In another embodiment, the pet food compositions disclosed herein comprise at least one MCT and/or at least one omega-3 fatty acid in the form of a supplement. Supplements include, for example, a feed or food used with another feed or food to improve the nutritive balance or performance of the total. Supplements can include compositions that are fed undiluted as a supplement to other feeds or foods, offered free choice with other parts of an animal's ration that are separately available, or diluted and mixed with an animal's regular feed or food to produce a complete feed or food. Supplements can be in various forms including, for example, powders, liquids (including gels), syrups, pills, encapsulated compositions, etc.

The pet food compositions disclosed herein may be wet or dry compositions, and the at least one MCT and/or at least one omega-3 fatty acid can be either incorporated into the food composition or on the surface of any composition component, such as, for example, by spraying, agglomerating, dusting, or precipitating on the surface.

In the pet food industry, for example, foods are generally classified as "wet" or "dry." A wet food has a relatively high amount of water and is usually present in a can or a container wherein air is substantially or totally excluded. Examples of such foods are "chunk and gravy," individual solid particles in the presence of liquid gravy or a loaf type material which generally takes the shape of the receptacle. A dry food is generally a baked or extruded material, the latter then cut into individual shaped portions, usually known as kibbles. The at least one MCT and/or the at least one omega-3 fatty acid can be readily incorporated into a wet or dry food through conventional means.

In preparing a pet food composition as disclosed herein in wet or canned form, any ingredient generally may, for example, be incorporated into the composition during the processing of the formulation, such as during and/or after mixing of other components of the composition. Distribution of these components into the composition may be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like) and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is may be accomplished by heating to temperatures of greater than about 230° F. (110° C.) for an appropriate time, which is dependent on, for example, the temperature used and the composition.

A pet food composition as disclosed herein may alternatively be prepared in a dry form using conventional processes. In certain embodiments, dry ingredients, including, for example, animal protein, plant protein, grains, etc., may be ground and mixed together. Moist or liquid ingredients, including fats, oils, animal protein, water, etc., may then added to and mixed with the dry mix. The mixture may then be processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

The pet food composition may be administered at a frequency and for a period of time effective to synergistically reduce at least one proinflammatory substance, such as at least one cytokine, in a companion animal that consumes the pet food composition. In certain embodiments, the composition is administered at least once daily, and in certain situations the composition is administered less frequent, such as twice weekly or weekly. In certain embodiments, administration may continue for at least about 1 week, for example at least about 2 weeks, at least about 3 weeks, at least about 1 month, at least about 2 months, at least about 3 months, at least about 4 months, at least about 5 months, at least about 6 months, at least about 1 year, at least about 2 years, or at least about 3 years. In one embodiment, administration continues from a time of initiation for substantially the remainder of the animal's life. Typically, the pet food composition is administered to the companion animal when the companion animal consumes the pet food composition.

The time of initiation can be at any stage of the animal's life, as there is no upper or lower age limit for initiating administration. For example, in the case of canine and feline companion animals, administration can be initiated when the animal is at least about 0.25, at least about 0.5, at least about 0.75, at least about 1, at least about 2, at least about 3, at least about 4, at least about 5, at least about 6, at least about 7, at least about 8, at least about 9, or at least about 10 years old. In one embodiment, administration is initiated at or near birth.

Also disclosed herein are methods for treating or preventing inflammation or an inflammatory disorder in a companion animal in need thereof, comprising administering to the companion animal a pet food composition comprising an effective amount of at least one MCT, such as caprylic acid and capric acid, and an effective amount of at least one omega-3 fatty acid, such as DHA and EPA, wherein the administration of the pet food composition results in a synergistic decrease in the amount of cytokines in the companion animal.

Further disclosed herein are methods for treating or preventing age-related disorders in a companion animal in need thereof, comprising administering to the companion animal in need thereof a pet food composition comprising an effective amount of at least one MCT, such as caprylic acid and capric acid, and an effective amount of at least one omega-3 fatty acid, such as DHA and EPA, wherein the administration of the pet food composition results in a synergistic increase in the levels of circulating carnitine and/or ALCAR derivative levels in the companion animal.

Further disclosed herein are methods for treating or preventing renal, gastrointestinal, and/or dermatological disorders in a companion animal in need thereof, comprising administering to the companion animal in need thereof an effective amount of at least one MCT, such as caprylic acid and capric acid, and an effective amount of at least one omega-3 fatty acid, such as DHA and EPA, wherein the administration of the pet food composition results in a synergistic decrease in the level of postbiotics, such as for example, indole derivatives, sulfated hologenomic metabolites, and phenolic derivatives.

The term "preventing" a disorder herein refers to preventing or decreasing the likelihood of developing a disorder, and the term "treating" refers to decreasing, ameliorating, or eliminating symptoms of the disorder.

Also disclosed herein are methods for selecting a composition for administration to an animal comprising making an assessment of the presence or absence of an inflammatory condition in the animal and selecting a composition based on the assessment, wherein if the assessment indicates the presence of an inflammatory condition, the pet food composition selected is one comprising an effective amount of at least one MCT and at least one omega-3 fatty acid present in an amount that is effective to prevent, ameliorate or treat the inflammatory condition.

In one embodiment disclosed herein, assessing comprises determining whether the animal has symptoms of such an inflammatory condition. In another embodiment, assessing comprises determining a level of a proinflammatory substance in a tissue or body fluid of an animal. For example, the level can be determined using a body fluid sample taken from the animal. Illustratively, a blood sample can be drawn from an animal and the level of a proinflammatory substance determined in the blood or serum from the sample.

A level of a proinflammatory substance can be determined in a body fluid sample using standard assays known in the art. For example, an assay may be chosen based on the type of proinflammatory substance being determined as well as the assay's suitability for quantifying the level of the substance in a particular sample. For example, a commercially available immunoassay utilizing monoclonal antibodies reactive to one or more epitopes on polypeptides or a competitive binding assay can be used for determining the serum level of a proinflammatory substance that is a protein. Alternatively, the level of such a proinflammatory substance may be determined by quantifying the level of its mRNA in cells that express the mRNA and which are present in the body fluid sample. Alternatively, the level of a proinflammatory substance can be determined by measuring activity level of the substance.

In some embodiments, a level is determined using one or more assays independently selected from the group consisting of enzyme immunoassays (EIAs), enzyme-linked immunosorbent assays (ELISAs), immunofluorescent assays (IFAs), radioimmunoassays (RIAs), western blot assays, northern blots, biochemical assays, enzymatic assays, and colorimetric assays. A variety of labels and conjugation techniques are known by those skilled in the art and can be used in the various biochemical, nucleic acid and amino acid assays. In certain embodiments, circulating cytokines may be assessed by ELISA.

A level of a proinflammatory substance can be an "observed" level that is compared to a reference level for the particular proinflammatory substance. For example, a reference level can be determined in a reference animal known not to have an inflammatory condition. A reference animal (i.e., the animal used to determine a reference level of a proinflammatory substance) will generally be of the same species, optionally of the same breed and/or of about the same age, as the animal for which the observed level is obtained. In certain embodiments, a reference elevated level can be determined by incorporating a sample of LPS from a gram-negative bacteria known to enhance the proinflammatory process. It is known that even clinically healthy populations of animals may have measurable levels of cytokines known to participate in the proinflammatory process. Reduction in levels of cytokines in this clinically healthy population may be assessed. Furthermore, levels of cytokines in an animal population suffering from chronic or acute inflammation conditions may also be assessed.

In some embodiments, the present invention provides a pet food composition for treating or preventing struvite urolithiasis in a companion animal comprising: at least one of caprylic acid and capric acid present in an amount ranging from about 1% to about 7%; and at least one of DHA and EPA present in an amount ranging from about 0.2% to about 3% by weight based on the total weight of the pet food composition, wherein the at least one of caprylic acid and capric acid and the at least one of DHA and EPA provide a synergistic decrease in an amino acid, or a precursor thereof, having pro-urolithiasis properties.

In some embodiments, the companion animal is selected from a cat and a dog. In other embodiments, the companion animal is a cat.

In some embodiments, the effective amount of the at least one of caprylic acid and capric acid is about 7% by weight based on the total weight of the pet food composition.

In other embodiments, the effective amount of the at least one of DHA and EPA ranges from about 2% to about 3% by weight based on the total weight of the pet food composition. In further embodiments, the ratio of DHA to EPA is at least about 7:1. In some embodiments, the at least one of DHA and EPA is added to the composition in the form of fish oil.

In yet other embodiments, the at least one of caprylic acid and capric acid is added to the composition in the form of an oil chosen from coconut oil, palm oil, and palm kernel oil.

Other embodiments of the present invention provide methods for treating or preventing struvite urolithiasis in a companion animal in need thereof, comprising: administering to the companion animal in need thereof a pet food composition comprising an effective amount of at least one of caprylic acid and capric acid; and an effective amount of at least one of DHA and EPA. In some embodiments, administration of the pet food composition to the companion animal results in a synergistic decrease in an amino acid, or a precursor thereof, having pro-urolithiasis properties.

In some embodiments, the amino acid, or precursor thereof, having pro-urolithiasis properties is selected from felinine (FLN); gamma-glutamylfelininylglycine (GG-FLN-GLY); felininylglycine (FLN-GLY); and a combination of two or more thereof. In some embodiments, administration of the pet food composition results in a synergistic decrease in a precursor of an amino acid having pro-urolithiasis properties. In other embodiments, the precursor of an amino acid having pro-urolithiasis properties is selected from gamma-glutamylfelininylglycine (GG-FLN-GLY); and felininylglycine (FLN-GLY).

In some embodiments, the present invention provides a method of reducing the level of a sulfur-containing amino acid in a companion animal, comprising administering to the companion animal an effective amount of a composition comprising: at least one of caprylic acid and capric acid in an amount of from about 1% to about 7%; and at least one of DHA and EPA in an amount of from about 0.2% to about 3% by weight based on the total weight of the pet food composition.

In other embodiments, the sulfur-containing amino acid is selected from: S-adenosylhomocysteine (SAH); cystathionine (CYST); glutathione disulfide (GSSG); cysteine-glutathione disulfide (CYSSG); and a combination of two or more thereof.

In some embodiments, the present invention provides a method of increasing the level of a sulfur-free byproduct in a companion animal, comprising administering to the companion animal an effective amount of a composition comprising: at least one of caprylic acid and capric acid in an amount of from about 1% to about 7%; and at least one of DHA and EPA in an amount of from about 0.2% to about 3% by weight based on the total weight of the pet food composition. In some embodiments, the sulfur-free byproduct is selected from: opthalmate (OPH); pyroglutamine (pGLN); and a combination thereof.

Still further embodiments provide a method of reducing the risk of renal stone formation in a companion animal, comprising administering to the companion animal an effective amount of a composition comprising: at least one of caprylic acid and capric acid in an amount of from about 1% to about 7%; and at least one of DHA and EPA in an amount of from about 0.2% to about 3% by weight based on the total weight of the pet food composition.

Yet other embodiments provide a method of reducing the level of a sulfur-containing amino acid and increasing the level of a sulfur-free byproduct in a companion animal, comprising administering to the companion animal an effective amount of a composition comprising: at least one of caprylic acid and capric acid in an amount of from about 1% to about 7%; and at least one of DHA and EPA in an amount of from about 0.2% to about 3% by weight based on the total weight of the pet food composition.

In some embodiments, disclosed herein are kits suitable for administering a pet food composition comprising at least one MCT and at least one omega-3 fatty acid to an animal. The kits may comprise in separate containers in a single package or in separate containers in a virtual package, as appropriate, at least one MCT, at least one omega-3 fatty acid, and at least one of (1) one or more ingredients suitable for consumption by an animal, (2) instructions for how to combine the at least one MCT, the at least one omega-3 fatty acid and other kit components to produce a composition useful for reducing the amount of a proinflammatory substance present at an elevated level in animal tissue or body fluid, and (3) instructions for how to use the at least one MCT, the at least one omega-3 fatty acid and other components of the present invention, particularly for the benefit of the animal. When the kit comprises a virtual package, the kit may be limited to instructions in a virtual environment in combination with one or more physical kit components. The kit may comprise the at least one MCT, the at least one omega-3 fatty acid, and other components in amounts sufficient to produce a pet food composition useful for reducing the amount of a proinflammatory substance present at an elevated level in animal tissue or body fluid. The kit may further comprise additional items such as a device for mixing the at least one MCT, the at least one omega-3 fatty acid, and ingredients or a device for containing the admixture, e.g., a food bowl.

EXAMPLES

Example 1

A diet was formulated and produced via extrusion to determine whether the inclusion of MCT and fish oil together would provide benefits not only to chronic inflammatory status, but also provide benefits in an ex vivo model of dysbiosis-induced inflammation.

Diets were formulated according to American Association of Feed Control Officials (AAFCO) and National Research Council (NRC) nutrition recommendations. The finished kibble was produced by extrusion, dried, and coated with palatants. In diets containing experimental fish oil and/or MCT, the oils were coated onto the exterior of dried kibble along with palatants. All diets were feline maintenance formulations. A Control Diet contained only the nutritional components of the formulation without the experimental oils (no fish or MCT, termed "None Diet"). Two additional Control Diets contained either MCT or fish oil and were labeled "MCT Diet" and "FO Diet," respectively. The Test Diet (termed "Both Diet"), in contrast, contained both experimental oils at the same levels found individually in the MCT and FO Control Diets (i.e., 7% and 2.85%, respectively). All diets are characterized in Table 1 below.

TABLE 1

Diet Formulations Comparison

| Ingredient Description | NONE DIET | FO DIET | MCT DIET | BOTH DIET |
|---|---|---|---|---|
| Corn, gluten, meal | 29 | 29 | 29 | 29 |
| Wheat, red, whole | 27.713 | 27.713 | 27.713 | 27.713 |
| Pork fat, choice white grease | 14.78 | 11.93 | 7.78 | 4.93 |
| Chicken dried 10% ash, chicken meal, and chicken liver digest | 15.5 | 15.5 | 15.5 | 15.5 |
| Beet, pulp, pelleted | 2.5 | 2.5 | 2.5 | 2.5 |
| Rice, brown | 2.35 | 2.35 | 2.35 | 2.35 |
| Calcium sulfate | 1.72 | 1.72 | 1.72 | 1.72 |

TABLE 1-continued

| Diet Formulations Comparison | | | | |
|---|---|---|---|---|
| Ingredient Description | NONE DIET | FO DIET | MCT DIET | BOTH DIET |
| Lactic acid, blend 84% | 1.2 | 1.2 | 1.2 | 1.2 |
| Palatants | 2 | 2 | 2 | 2 |
| Potassium, sodium, and choline chloride | 1.861 | 1.861 | 1.861 | 1.861 |
| Soybean oil, crude, degummed | 0.5 | 0.5 | 0.5 | 0.5 |
| Vitamin E, oil, 29% | 0.43 | 0.43 | 0.43 | 0.43 |
| Taurine | 0.174 | 0.174 | 0.174 | 0.174 |
| Vitamin and mineral premixes | 0.212 | 0.212 | 0.212 | 0.212 |
| Oat fiber, fruit, vegetable blend | 0.04 | 0.04 | 0.04 | 0.04 |
| Fish oil MEG-3 0355TG oil | — | 2.85 | — | 2.85 |
| Captex ® 355 Medium Chain Triglyceride | — | — | 7 | 7 |

An Institutional Animal Care and Use Committee (IACUC) approved dietary intervention protocol was implemented with enrolled healthy feline subjects randomized to four groups based on age, weight, and sex. Cats were assessed as healthy by markers of biochemical and clinical health. The study was caretaker-blinded, longitudinal design in a 2×2 design (+/−FO, +/−MCT).

Example 2

Circulating cytokines were assessed by enzyme-linked immunosorbent assay (ELISA) in multiplex format and expressed in picograms per milliliter (pg/ml). Whole blood ex vivo culture was performed on blood drawn from fed cats. Two blood culture tubes were drawn from each cat that had been fed one of the four experimental diets for 28 days. One tube contained blood culture media to sustain blood cell activity (Chronic tube). The second tube contained this same media and the addition of a component of gram negative bacteria that is known to be increased in the blood during gut microbiome dysbiosis and loss of gut barrier integrity (Dysbiosis tube). In the Chronic tube, whole blood was left unperturbed to continue metabolic and immune processes set in place by the state of the cat's nutrition prior to the blood draw. Although an overtly clinically healthy population, all cats had measurable levels of cytokines known to participate in pro-inflammatory processes. Reduction in levels of cytokines in the unperturbed Chronic tubes indicated a decreased chronic pro-inflammatory state in cats. When levels of cytokines were reduced in the Dysbiosis tube, which contained products mimicking bacterial dysbiosis, this indicated that inflammation in cats in response to microbiome imbalance was decreased. Of particular note are the instances when a diet reduced cytokines in both Chronic and Dysbiosis tubes, as that indicated the diet reduced inflammation in both chronic and acute instances.

Both the Control Diets and the Test Diet retained the same overt nutritional qualities while varying in their inclusion of fish oil and/or MCT, the sources of EPA/DHA and caprylic acid and capric acid, respectively. All diets were formulated to the same following predicted values (dry matter basis except moisture): fat (22.2 g/100 g), protein (35.1 g/100 g), nitrogen free extract (33.7 g/100 g), fiber (7 g/100 g), ash (7.4 g/100 g), and moisture (7.5 g/100 g), with Atwater energy (4300 kcal/kg). Since there were no foreseeable differences in the macronutrient makeup, nor were their qualitative differences in the ingredients other than the experimental oils, it was proposed that all anti-inflammatory effects documented herein were due to the unique properties of these oils.

Table 2 below outlines the anti-inflammatory effects of the combination of fish oil and MCT (the Both Diet) in the case relative to chronic inflammation. Comparing cytokine levels in Chronic tubes drawn from cats fed these oils to cytokine levels in tubes drawn from cats fed the None Diet or the FO Diet or MCT Diet individually, shows that combining the MCT and fish oil (Both Diet) had an effect that surpassed either the FO Diet or the MCT Diet individually. In 6 out of 7 cytokines reported, namely Fas, GM-CSF, IL-2, IL-13, IL-18, and SDF-1, a synergistic effect was observed. The Both Diet reduced levels of cytokines below levels seen in either the FO Diet or the MCT Diet fed cats. Further, Table 2 also indicates that for these same 6 cytokines, the levels observed were lower than the levels calculated by adding the individual effects of FO Diet and MCT Diet together; thus, a synergistic anti-inflammatory effect is manifest in the chronic condition.

TABLE 2

Cytokine Levels of Unstimulated Cells in CHRONIC tubes

| | | Individual Levels | | | | Individual Effects | | | Additive Effect | Enhanced Synergistic Effect of BOTH Diet (((BOTH − NONE) − ((FO − NONE) + |
|---|---|---|---|---|---|---|---|---|---|---|
| Cytokines | Statistic | NONE | FO | BOTH | MCT | BOTH − NONE | FO − NONE | MCT − NONE | (FO − NONE) + (MCT − NONE) | (MCT − NONE)))/ NONE)*100 |
| Fas | Mean | 4.10 | 5.21 | 3.24 | 3.62 | −0.86 | 1.11 | −0.48 | 0.64 | −36.60 |
| | Std Err | 1.33 | 2.00 | 1.08 | 1.29 | | | | | |
| GM-CSF | Mean | 2.48 | 2.98 | 1.81 | 2.42 | −0.67 | 0.50 | −0.06 | 0.44 | −44.68 |
| | Std Err | 0.36 | 0.76 | 0.22 | 0.33 | | | | | |
| IL-2 | Mean | 2.88 | 3.11 | 2.13 | 3.73 | −0.75 | 0.23 | 0.85 | 1.08 | −63.60 |
| | Std Err | 0.26 | 0.28 | 0.35 | 0.32 | | | | | |
| IL-13 | Mean | 8.35 | 8.60 | 5.36 | 7.27 | −2.99 | 0.25 | −1.08 | −0.82 | −25.91 |
| | Std Err | 1.90 | 2.13 | 0.71 | 1.56 | | | | | |
| IL-8 | Mean | 35.96 | 40.04 | 8.12 | 11.06 | −27.84 | 4.08 | −24.90 | −20.82 | −19.53 |
| | Std Err | 13.68 | 25.55 | 1.54 | 4.58 | | | | | |
| SDF-1 | Mean | 133.38 | 76.95 | 20.29 | 97.26 | −113.09 | −56.43 | −36.13 | −92.56 | −15.40 |
| | Std Err | 36.64 | 21.50 | 11.25 | 29.53 | | | | | |
| TNFalpha | Mean | 27.03 | 26.33 | 20.88 | 13.62 | −6.15 | −0.71 | −13.42 | −14.13 | 29.49 |
| | Std Err | 8.73 | 6.65 | 7.48 | 2.76 | | | | | |

Table 3 outlines the anti-inflammatory effects of the combination of fish oil and MCT (the Both Diet) in the case relative to inflammation that can be induced by loss of gut barrier integrity and increased microbiome dysbiosis. Comparing cytokine levels in Dysbiosis tubes drawn from cats fed these oils to cytokine levels from cats fed the None Diet or the FO Diet or MCT Diet individually, shows that the combination of fish oil and MCT has an effect that surpasses either oil individually. In 6 out of 7 cytokines reported, namely Fas, GM-CSF, IL-2, IL-13, SDF-1, and TNFα. The Both Diet reduced levels of cytokines below levels seen in either the FO Diet or the MCT Diet fed cats. Further, Table 3 also indicates that for all 7 cytokines, the levels observed were lower than the levels calculated by adding the individual effects of the FO Diet and MCT Diet together; thus, a synergistic anti-inflammatory effect is also manifest in the dysbiosis condition, as observed for the chronic condition.

TABLE 3

Cytokine Levels of Stimulated Cells in Dysbiosis tubes

| | | Individual Levels | | | | Individual Effects | | | Additive Effect | Enhanced Synergistic Effect of BOTH Diet (((BOTH − NONE) − ((FO − NONE) + |
|---|---|---|---|---|---|---|---|---|---|---|
| | | | | | | BOTH − | FO − | MCT − | (FO − NONE) + | (MCT − NONE)))/ |
| Cytokines | Statistic | NONE | FO | BOTH | MOT | NONE | NONE | NONE | (MCT − NONE) | NONE)*100 |
| Fas | Mean | 4.78 | 6.35 | 3.99 | 4.55 | −0.79 | 1.57 | −0.24 | 1.33 | −44.47 |
| | Std Err | 1.50 | 2.33 | 1.33 | 1.74 | | | | | |
| GM-CSF | Mean | 3.07 | 4.17 | 1.81 | 3.45 | −1.26 | 1.10 | 0.38 | 1.48 | −89.26 |
| | Std Err | 0.44 | 1.06 | 0.22 | 0.75 | | | | | |
| IL-2 | Mean | 3.16 | 4.92 | 2.29 | 4.26 | −0.88 | 1.76 | 1.10 | 2.85 | −117.93 |
| | Std Err | 0.36 | 0.91 | 0.47 | 0.63 | | | | | |
| IL-13 | Mean | 8.78 | 9.07 | 5.54 | 7.72 | −3.24 | 0.29 | −1.06 | −0.77 | −28.11 |
| | Std Err | 1.98 | 2.18 | 0.75 | 1.76 | | | | | |
| IL-8 | Mean | 2776.99 | 2962.83 | 2591.47 | 2473.35 | −185.53 | 185.83 | −303.64 | −117.81 | −2.44 |
| | Std Err | 360.45 | 331.40 | 268.72 | 328.72 | | | | | |
| SDF-1 | Mean | 164.87 | 108.01 | 20.98 | 116.16 | −143.89 | −56.86 | −48.70 | −105.56 | −23.25 |
| | Std Err | 42.46 | 27.81 | 11.07 | 32.22 | | | | | |
| TNF-α | Mean | 207.49 | 199.81 | 173.54 | 200.66 | −33.96 | −7.68 | −6.83 | −14.51 | −9.37 |
| | Std Err | 24.94 | 24.15 | 27.48 | 41.81 | | | | | |

In sum, a test diet matched with three other control diets to control for macronutrient profile as well as individual and additive effects of two experimental oils produced synergistic decreases in pro-inflammatory cytokines in a manner greater than could be predicted by either experimental oil alone. This effect was surprising and unexpected, impacting inflammation in both chronic and dysbiosis models.

Example 3

A global metabolomics screen was performed on serum samples drawn from each cat that had been fed one of the four experimental diets for 28 days. In brief, serum was lyophilized and extracted with methanol:water to liberate metabolites from serum matrix. Metabolomics was performed by LC-MS with relative fold quantitation. Values presented indicate natural logarithm transform of relative levels of a given metabolite circulating in cats fed a particular food.

The Both Diet profoundly decreased levels of circulating postbiotics in cats after 28 days. Statistical analysis by multivariate analysis of variance (MANOVA) showed the differences observed between groups were significant at a=0.05 ($P<0.05$). Class analysis of the various types of postbiotics indicated that the Both Diet significantly decreased each class, including indoles, hologenomic sulfates (products of the metabolism of both microbes and feline hosts), and phenolics. Tables 4-6 quantify the synergism exhibited; the rightmost column of each table provides the difference of the effects with the Both Diet compared to the differences of the individual oils summed (FO Diet+MCT Diet). It is readily apparent that the Both Diet uniformly and profoundly (this is a natural log scale) synergized to decrease circulating postbiotics, including indoles, hologenomic sulfates, and phenolics, in a manner not reproduced by separate additive effects of the FO Diet and MCT Diet.

In summary, a test diet matched with three other control diets to control for macronutrient profile as well as individual and additive effects of two experimental oils produced consistent and significant decreases in levels of circulating postbiotics of several classes known to impact renal, gastrointestinal and dermatological diseases.

TABLE 4

Indole Levels in Serum of Cats Fed Control and Test Diets

| Postbiotic Indole | Control | DBA | MCT | DHA/MCT | DHA − Cntl | MCT − Cntl | DHA/ MCT − Cntl | (DHA − Cntl) + (MCT − Cntl) | (DHA/ MCT − Cntl) − ((DHA − Cntl) + MCT − Cntl)) |
|---|---|---|---|---|---|---|---|---|---|
| 2-oxindole-3-acetate T-28-2-oxindole-3-acetate P-14 | 0.17 | 0.23 | −0.05 | −0.67 | 0.06 | −0.22 | −0.84 | −0.17 | −0.67 |
| 3-hydroxyindolin-2-one sulfate T-28-3-hydroxyindole-2-one sulfate P-14 | 0.02 | 0.22 | 0.13 | −0.22 | 0.19 | 0.11 | −0.24 | 0.30 | −0.54 |
| 5-hydroxyindole sulfate T-28-5-hydroxyindole sulfate P-14 | −0.07 | 0.22 | −0.17 | −0.47 | 0.29 | −0.10 | −0.40 | 0.19 | −0.59 |
| 6-hydroxyindole sulfate T-28-6-hydroxyindole sulfate P-14 | −0.03 | 0.30 | −0.07 | −0.36 | 0.33 | −0.04 | −0.33 | 0.29 | −0.62 |
| 7-hydroxyindole sulfate T-28-7-hydroxyindole sulfate P-14 | −0.05 | −0.10 | 0.00 | −0.40 | −0.06 | 0.05 | −0.35 | −0.01 | −0.35 |
| Indole-3-carboxylic acid T-28-indole-3-carboxylic acid P-14 | −0.12 | 0.43 | 0.30 | 0.03 | 0.55 | 0.42 | 0.15 | 0.97 | −0.82 |
| Indoleacetate T-28-indoleacetate P-14 | 0.18 | 0.36 | −0.17 | −0.54 | 0.18 | −0.35 | −0.73 | −0.17 | −0.56 |
| Indoleacetylglutamine T-28-indoleacetylglutamine P-14 | −0.09 | 0.08 | 0.04 | −0.90 | 0.16 | 0.13 | −0.81 | 0.29 | −1.10 |
| Indoleacetylglglycine T-28-indoleacetylglycine P-14 | −0.02 | 0.05 | −0.18 | −0.76 | 0.07 | −0.16 | −0.74 | −0.08 | −0.66 |
| Indoleacrylate T-28-indoleacrylate P-14 | 0.11 | 0.66 | 0.13 | −0.31 | 0.56 | 0.02 | −0.41 | 0.58 | −0.99 |
| Indoleacetate T-28-indoleacetate P-14 | −0.02 | −0.14 | −0.10 | −0.48 | −0.12 | −0.08 | −0.46 | −0.20 | −0.25 |
| Indolepropionate T-28-indolepropionate P-14 | 0.03 | 0.56 | 0.06 | −0.43 | 0.53 | 0.03 | −0.46 | 0.56 | −1.02 |
| Indole-2-one T-28-indole-2-one P-14 | 0.19 | 0.20 | −0.33 | −0.49 | 0.01 | −0.52 | −0.68 | −0.51 | −0.17 |

TABLE 5

Hologenomic Sulfate Levels in Serum of Cats Fed Control and Test Diets

| Postbiotic Hologenomic Sulfate | Control | DHA | MCT | DHA/MCT | DHA − Cntl | MCT − Cntl | DHA/ MCT − Cntl | (DHA − Cntl) + (MCT − Cntl) | (DHA/ MCT − Cntl) − ((DHA − Cntl) + MCT − Cntl)) |
|---|---|---|---|---|---|---|---|---|---|
| 2-aminophenol sulfate T-28-2-aminophenol sulfate P-14 | −0.02 | 0.47 | −0.01 | −0.80 | 0.48 | 0.01 | −0.78 | 0.49 | −1.27 |
| 3-(3-hydroxyphenol)propionate sulfate T-28-3-(3-hydroxyphenol)propionate sulfate P-14 | 0.04 | 0.84 | −0.19 | −1.46 | 0.79 | −0.23 | −1.51 | 0.56 | −2.07 |
| 4-acetylphenyl sulfate T-28-4-acetylphenyl sulfate P-14 | −0.08 | 0.33 | −0.14 | −0.49 | 0.41 | −0.06 | −0.42 | 0.35 | −0.77 |
| 3-methoxycatechol sulfate (2) T-28-3-methoxycatechol sulfate (2) P-14 | 0.14 | 0.18 | 0.10 | −0.85 | 0.04 | −0.04 | −0.99 | 0.00 | −0.99 |
| 4-ethylphenyl sulfate T-28-4-ethylphenyl sulfate P-14 | 0.09 | 0.21 | 0.21 | −0.88 | 0.12 | 0.12 | −0.97 | 0.24 | −1.21 |
| 4-hydroxycinnamate sulfate T-28-4-hydroxycinnamate sulfate P-14 | 0.10 | 0.96 | −0.25 | −0.77 | 0.86 | −0.35 | −0.87 | 0.51 | −1.38 |
| 4-methylcatechol sulfate T-28-4-methylcatechol sulfate P-14 | 0.02 | 0.30 | 0.20 | −0.68 | 0.29 | 0.18 | −0.70 | 0.46 | −1.16 |
| 4-vinylguaiacol sulfate T-28-4-vinylguaiacol sulfate P-14 | −0.40 | −0.60 | 0.04 | −1.44 | −0.21 | 0.44 | −1.04 | 0.23 | −1.27 |
| 4-vinylphenol sulfate T-28-4-vinylphenol sulfate P-14 | −0.29 | −0.14 | 0.03 | −1.43 | 0.15 | 0.32 | −1.14 | 0.47 | −1.61 |
| Hydroquinone sulfate T-28-hydroquinone sulfate P-14 | 0.10 | 0.49 | 0.16 | −0.46 | 0.39 | 0.06 | −0.57 | 0.45 | −1.01 |
| Isoeugenol sulfate T-28-isoeugenol sulfate P-14 | 0.11 | −0.35 | 0.23 | −0.77 | −0.46 | 0.12 | −0.89 | −0.34 | −0.54 |
| Equol sulfate T-28-equol sulfate P-14 | 0.30 | 0.19 | −0.07 | −0.45 | −0.10 | −0.36 | −0.74 | −0.46 | −0.28 |
| O-methylcatechol sulfate T-28-O-methylcatechol sulfate P-14 | 0.13 | 0.85 | −0.26 | −0.93 | 0.72 | −0.39 | −1.06 | 0.33 | −1.39 |

TABLE 6

Phenolic Levels in Serum of Cats Fed Control and Test Diets

| Postbiotic Phenolic | Control | DHA | MCT | DHA/MCT | DHA − Cntl | MCT − Cntl | DHA/ MCT − Cntl | (DHA − Cntl) + (MCT − Cntl) | ((DHA/ MCT − Cntl) − ((DHA − Cntl) + MCT − Cntl)) |
|---|---|---|---|---|---|---|---|---|---|
| 2-hydroxyphenylacetate T-28-2-hydroxyphenylacetate P-14 | −0.03 | 0.04 | −0.14 | −0.12 | 0.07 | −0.11 | −0.08 | −0.04 | −0.04 |
| 3-(3-hydroxyphenyl)propionate T-28-3-(3-hydroxyphenyl)propionate P-14 | −0.11 | 0.40 | −0.23 | −1.03 | 0.51 | −0.13 | −0.92 | 0.38 | −1.30 |
| 3-(4-hydroxyphenyl)lactate (HPLA) T-28-3-(4-hydroxyphenyl)lactate (HPLA) P-14 | −0.05 | −0.13 | −0.09 | −0.20 | −0.08 | −0.04 | −0.16 | −0.12 | −0.03 |
| 3-(4-hydroxyphenyl)propionate T-28-3-(4-hydroxyphenyl)propionate P-14 | −0.09 | 0.40 | −0.31 | −0.81 | 0.49 | −0.23 | −0.73 | 0.26 | −0.99 |
| 3-hydroxy-3-phenylpropionate T-28-3-hydroxy-3-phenylpropionate P-14 | −0.30 | −0.05 | 0.63 | 0.55 | 0.25 | 0.93 | 0.85 | 1.18 | −0.33 |
| 3-phenylpropionate (hydrocinnamate) T-28-3-phenylpropionate (hydrocinnamate) P-14 | 0.09 | 0.14 | 0.22 | −0.35 | 0.05 | 0.13 | −0.44 | 0.18 | −0.62 |
| 4-hydroxyphenylacetylglycine T-28-4-hydroxyphenylacetylglycine P-14 | −0.23 | −0.04 | −0.17 | −1.06 | 0.19 | 0.06 | −0.83 | 0.25 | −1.07 |
| 4-hydroxyphenylpryuvate T-28-4-hydroxyphenylpryuvate P-14 | 0.17 | −0.03 | 0.19 | −0.11 | −0.21 | 0.01 | −0.28 | −0.19 | −0.09 |
| Phenylacetate T-28-phenylacetate P-14 | 0.27 | 0.40 | 0.09 | −0.34 | 0.13 | −0.18 | −0.61 | −0.05 | −0.56 |
| Phenylacetylalanine T-28-phenylacetylalanine P-14 | 0.48 | −0.66 | −0.32 | −0.91 | −1.14 | −0.80 | −1.39 | −1.94 | 0.55 |
| Phenylacetylcarnitine T-28-phenylacetylcarnitine P-14 | 0.51 | 0.47 | −0.08 | 0.13 | −0.04 | −0.59 | −0.39 | −0.63 | 0.25 |
| Phenylacetylglutamate T-28-phenylacetylglutamate P-14 | 0.11 | 0.18 | −0.02 | −0.37 | 0.08 | −0.13 | −0.47 | −0.06 | −0.42 |
| Phenylacetylglutamine T-28-phenylacetylglutamine P-14 | 0.28 | 0.53 | 0.00 | −0.44 | 0.25 | −0.28 | −0.72 | −0.03 | −0.69 |
| Phenylacetylglycine T-28-phenylacetylglycine P-14 | 0.11 | 0.14 | −0.19 | −0.40 | 0.04 | −0.30 | −0.51 | −0.26 | −0.25 |
| Phenylacetylserine T-28-phenylacetylserine P-14 | 0.25 | −0.13 | −0.06 | −0.27 | −0.11 | −0.31 | −0.52 | −0.42 | −0.09 |
| Phenyllactate (PLA) T-28-phenyllactate P-14 | −0.02 | −0.17 | −0.08 | −0.27 | −0.16 | −0.07 | −0.25 | −0.23 | −0.03 |
| Phenylpropionylglycine T-28-phenylpropionylglycine P-14 | −0.27 | −0.01 | −0.32 | 0.28 | 0.25 | −0.05 | −0.01 | 0.20 | −0.21 |
| Phenylpyruvate T-28-phenylpyruvate P-14 | −0.01 | 0.22 | −0.09 | −0.32 | 0.24 | −0.07 | −0.31 | 0.16 | −0.47 |

Example 4

A global metabolomics screen was performed on serum samples drawn from each cat that had been fed one of the four experimental diets for 28 days. In brief, serum was lyophilized and extracted with methanol:water to liberate metabolites from serum matrix. Metabolomics was performed by LC-MS with relative fold quantitation. Values presented indicate natural logarithm transform of relative levels of a given metabolite circulating in cats fed a particular food.

The Both Diet dramatically and statistically significantly increased circulating carnitine. In contrast, the MCT Diet and the FO Diet were incapable of modulating carnitine. Further, blood brain barrier-permeable carnitine derivative ALCAR increased as well with the Both Diet, but not with either the MCT Diet or the FO Diet. Statistical analysis by multivariate analysis of variance (MANOVA) showed the differences observed between groups were significant at a=0.05 ($P<0.05$). Table 7 quantifies the synergism observed. The rightmost column provides the difference of the effects with the Both Diet compared to the differences of the individual oils summed (MCT Diet+FO Diet). It is readily apparent that the Both Diet synergized to increase circulating carnitine conjugates in a manner not reproduced by separate additive effects of MCT Diet and the FO Diet.

In summary, a test diet matched with three other control diets to control for macronutrient profile as well as individual and additive effects of two experimental oils produced increased levels of circulating carnitine conjugates of several classes known to impact metabolic functions.

TABLE 7

Carnitine Levels in Serum of Cats Fed Control and Test Diets

| Carnitine Conjugate | Control | DHA | MCT | DHA/MCT | DHA − Cntl | MCT − Cntl | DHA/MCT − Cntl | (DHA − Cntl) + (MCT − Cntl) | (DHA/MCT − Cntl) − ((DHA − Cntl) + MCT − Cntl)) | % Synergistic Enhancement |
|---|---|---|---|---|---|---|---|---|---|---|
| Docosahexanoylcarnitine (C22:6) | −0.34 | 2.23 | 0.08 | 1.75 | 2.57 | 0.42 | 2.09 | 2.99 | −0.09 | −59.33 |
| Docosapentanoylcartinme (C22:5n3) | −0.31 | 0.82 | −0.05 | 0.78 | 1.13 | 0.26 | 1.10 | 1.40 | −0.30 | −25.98 |
| Decanoylcaritine (C10) | −0.32 | 0.07 | 0.55 | 0.54 | 0.39 | 0.87 | 0.97 | 1.26 | −0.29 | −25.31 |
| Dihomo-linolenoylcarnitine (C20:3n3 or 6) | −0.10 | 0.36 | 0.07 | 0.35 | 0.46 | 0.17 | 0.45 | 0.63 | −0.18 | −16.57 |
| Octadecenedioylcarnitine (C18:1-DC) | −0.09 | 0.60 | −0.08 | 0.53 | 0.70 | 0.01 | 0.63 | 0.71 | −0.08 | −8.06 |
| Butyrylcarnitine (C4) | −0.11 | −0.15 | 0.17 | 0.10 | −0.04 | 0.28 | 0.21 | 0.24 | −0.02 | −2.32 |
| Laurylcarnitine (C12) | −0.17 | 0.21 | 0.07 | 0.44 | 0.38 | 0.25 | 0.61 | 0.63 | −0.01 | −1.26 |
| Nervonoylcarnitine (C24:1) | −0.13 | 0.53 | −0.17 | 0.48 | 0.66 | −0.04 | 0.61 | 0.62 | −0.01 | −0.92 |
| 5-dodecenoylcarnitine (C12:1) | −0.20 | 0.23 | 0.06 | 0.50 | 0.42 | 0.26 | 0.70 | 0.68 | 0.01 | 1.29 |
| Myristoyleoylcarnitine (C14:1) | −0.19 | 0.33 | 0.04 | 0.58 | 0.52 | 0.23 | 0.77 | 0.74 | 0.02 | 2.31 |
| Margaroylcarnitine (C17) | −0.11 | 0.10 | −0.04 | 0.02 | 0.21 | 0.07 | 0.31 | 0.28 | 0.03 | 3.06 |
| Cerotoylcarnitine (C26) | −0.17 | 0.07 | −0.58 | −0.31 | 0.23 | −0.42 | −0.14 | −0.18 | 0.04 | 4.17 |
| Arachidonoylcarnitine (C20:4) | −0.08 | 0.38 | −0.09 | 0.44 | 0.46 | −0.01 | 0.52 | 0.46 | 0.06 | 6.39 |
| Palmitoleoylcarnitine (C16:1) | −0.13 | 0.20 | 0.00 | 0.41 | 0.33 | 0.14 | 0.55 | 0.47 | 0.08 | 7.83 |
| Linolenoylcaraitiue (C18:3) | −0.13 | −0.13 | −0.07 | 0.03 | 0.01 | 0.06 | 0.17 | 0.07 | 0.10 | 10.02 |
| Succinylcarnitine (C4) | −0.06 | 0.03 | −0.02 | 0.17 | 0.10 | 0.04 | 0.24 | 0.14 | 0.10 | 10.04 |
| Deoxycarnitine | −0.06 | −0.08 | −0.05 | 0.05 | −0.02 | 0.01 | 0.11 | −0.01 | 0.12 | 12.56 |
| Octonoylcarnitine (C8) | −0.24 | 0.07 | 0.15 | 0.58 | 0.31 | 0.39 | 0.82 | 0.70 | 0.12 | 12.95 |
| Cis-4-decenoylcarnitine (C10:1) | −0.10 | 0.20 | 0.41 | 0.85 | 0.31 | 0.52 | 0.95 | 0.82 | 0.13 | 13.48 |
| Benzoylcarnitine | −0.06 | 0.27 | −0.32 | 0.03 | 0.20 | −0.38 | −0.03 | −0.17 | 0.14 | 15.17 |
| Lignoceroylcarnitine (C24) | −0.15 | 0.08 | −0.46 | −0.09 | 0.23 | −0.31 | 0.06 | −0.08 | 0.14 | 15.38 |
| Adipoylcarnitine (C6-DC) | −0.01 | 0.09 | 0.19 | 0.44 | 0.10 | 0.20 | 0.45 | 0.30 | 0.15 | 16.12 |
| Carnitine | −0.03 | 0.03 | 0.07 | 0.29 | 0.06 | 0.10 | 0.32 | 0.16 | 0.16 | 17.11 |
| Dihomo-linolenoylcarnitine (C20:2) | −0.09 | −0.25 | −0.09 | −0.09 | −0.16 | 0.00 | 0.00 | −0.16 | 0.16 | 17.20 |
| Myristoylcarnitine (C14) | −0.14 | −0.01 | −0.07 | 0.23 | 0.13 | 0.07 | 0.37 | 0.21 | 0.17 | 18.22 |
| Propionylcarnitine (C3) | 0.02 | 0.00 | −0.06 | 0.10 | −0.01 | −0.07 | 0.08 | −0.09 | 0.17 | 18.53 |
| Adrenoylcarnitine (C22:4) | −0.07 | −0.30 | −0.13 | −0.19 | −0.23 | −0.06 | −0.12 | −0.29 | 0.17 | 19.00 |
| Octadecanedioylcarnitine (C18-DC) | −0.09 | 0.61 | −0.08 | 0.80 | 0.70 | 0.02 | 0.90 | 0.72 | 0.18 | 19.27 |
| Behenoylcarnitine (C22) | −0.10 | 0.07 | −0.41 | −0.06 | 0.16 | −0.32 | 0.03 | −0.16 | 0.19 | 20.85 |
| Glutaroylcarnitine (C5) | −0.09 | −0.28 | −0.28 | −0.28 | −0.20 | −0.19 | −0.20 | −0.39 | 0.19 | 21.09 |
| Arachidoylcarnitine (C20) | −0.02 | −0.07 | −0.26 | −0.12 | −0.05 | −0.24 | −0.10 | −0.29 | 0.20 | 21.99 |
| Linoleoylcarnitine (C18:2) | −0.04 | −0.12 | −0.10 | 0.02 | −0.08 | −0.06 | 0.06 | −0.14 | 0.20 | 22.34 |
| Stearoylcarnitine (C18) | −0.02 | −0.17 | −0.09 | −0.02 | −0.14 | −0.06 | 0.00 | −0.21 | 0.21 | 23.13 |
| Palmitoylcarnitine | −0.05 | −0.05 | −0.12 | 0.11 | 0.00 | −0.07 | 0.15 | −0.07 | 0.22 | 25.22 |
| Pimeloylcarnitine/3-methyladipoylcarnitine (C7-DC) | −0.30 | 0.00 | −0.16 | 0.38 | 0.30 | 0.14 | 0.68 | 0.44 | 0.24 | 27.12 |
| Phenylacetylcarnitine | 0.51 | 0.47 | −0.08 | 0.13 | −0.04 | −0.59 | −0.39 | −0.63 | 0.25 | 27.87 |
| Eicosenoylcarnitine (C20:1) | −0.08 | −0.10 | −0.09 | 0.14 | −0.02 | −0.01 | 0.23 | −0.03 | 0.25 | 28.75 |
| Oleoylcarnitine (C18) | −0.06 | −0.05 | −0.08 | 0.19 | 0.01 | −0.02 | 0.25 | −0.01 | 0.26 | 29.69 |
| Suberoylcarnitine (C8-DC | −0.26 | −0.10 | −0.26 | 0.19 | 0.15 | 0.00 | 0.45 | 0.15 | 0.30 | 35.33 |
| Hexanoylcarnitine (C6) | −0.11 | 0.04 | 0.08 | 0.56 | 0.15 | 0.20 | 0.67 | 0.35 | 0.32 | 38.15 |
| Tiglyl carnitine (C5) | −0.05 | 0.02 | −0.26 | 0.16 | 0.08 | −0.21 | 0.22 | −0.13 | 0.35 | 41.80 |
| Isobutyrylcarnitine (C4) | 0.00 | −0.09 | −0.23 | 0.04 | −0.09 | −0.23 | 0.04 | −0.32 | 0.36 | 43.35 |
| 3-hydroxtbutyrylcarnitine (2) | −0.07 | 0.03 | −0.08 | 0.44 | 0.11 | 0.00 | 0.51 | 0.10 | 0.41 | 50.14 |
| Isovalerylcarnitine (C5) | 0.14 | 0.14 | 0.05 | 0.47 | −0.01 | −0.10 | 0.33 | −0.11 | 0.43 | 54.26 |
| Acetylcarnitine (C2) | −0.04 | 0.00 | −0.02 | 0.47 | 0.04 | 0.03 | 0.51 | 0.07 | 0.45 | 56.12 |
| 2-methylbutyroylcarnitine (C5) | 0.08 | −0.06 | −0.09 | 0.31 | −0.14 | −0.17 | 0.23 | −0.32 | 0.55 | 72.82 |
| Erucoylcarnitine (C22:1) | −0.18 | −0.10 | −0.19 | 0.48 | 0.08 | −0.01 | 0.66 | 0.07 | 0.59 | 80.00 |

What is claimed is:

1. A pet food composition for treating or preventing struvite urolithiasis in a cat comprising:

at least one of caprylic acid and capric acid present in an amount ranging from about 1% to about 7%; and at least one of DHA and EPA present in an amount of from about 0.2% to about 3% by weight based on the total weight of the pet food composition.

2. The pet food composition according to claim 1, wherein the at least one of caprylic acid and capric acid and the at least one of DHA and EPA provide a synergistic decrease in an amino acid, or a precursor thereof, having pro-urolithiasis properties.

3. The pet food composition according to claim 2, wherein the amino acid, or precursor thereof, having pro-urolithiasis properties is selected from felinine (FLN); gamma-glutamylfelininylglycine (GG-FLN-GLY); felininylglycine (FLN-GLY); or a combination of two or more thereof.

4. The pet food composition according to claim 2, wherein the precursor of the amino acid having pro-urolithiasis properties is selected from gamma-glutamylfelininylglycine (GG-FLN-GLY); felininylglycine (FLN-GLY); or a combination thereof.

5. The pet food composition according to claim 1, wherein the at least one of caprylic acid and capric acid and the at least one of DHA and EPA provide a synergistic decrease in a sulfur-containing amino acid.

6. The pet food composition according to claim 5, wherein the sulfur-containing amino acid is selected from: S-adenosylhomocysteine (SAH); cystathionine (CYST); glutathione disulfide (GSSG); cysteine-glutathione disulfide (CYSSG); or a combination of two or more thereof.

7. The pet food composition according to claim 1, wherein the at least one of caprylic acid and capric acid and the at least one of DHA and EPA provide a synergistic increase in the level of a sulfur-free byproduct.

8. The pet food composition according to claim 7, wherein the sulfur-free byproduct is selected from: opthalmate (OPH); pyroglutamine (pGLN); or a combination thereof.

9. The pet food composition according to claim 1, wherein the effective amount of the at least one of caprylic acid and capric acid is about 7% by weight based on the total weight of the pet food composition.

10. The pet food composition according to claim 1, wherein the effective amount of the at least one of DHA and EPA is from about 2% to about 3% by weight based on the total weight of the pet food composition.

11. The pet food composition according to claim 1, wherein DHA and EPA are present in a ratio of DHA to EPA that is at least about 7:1.

12. A method for treating or preventing struvite urolithiasis in a companion animal in need thereof, reducing the level of a sulfur-containing amino acid in a companion animal in need thereof, increasing the level of a sulfur-free byproduct in a companion animal in need thereof, or reducing the risk of renal stone formation in a companion animal in need thereof, the method comprising:

administering to the companion animal in need thereof a pet food composition comprising an effective amount of at least one of caprylic acid and capric acid; and an effective amount of at least one of DHA and EPA, wherein the administration of the pet food composition to the companion animal results in a synergistic decrease in an amino acid, or a precursor thereof, having pro-urolithiasis properties, and wherein the companion animal is a cat.

13. The method according to claim 12, wherein the amino acid, or precursor thereof, having pro-urolithiasis properties is selected from felinine (FLN); gamma-glutamylfelininylglycine (GG-FLN-GLY); felininylglycine (FLN-GLY); or a combination of two or more thereof.

14. The method according to claim 12, wherein the administration of the pet food composition results in a synergistic decrease in a precursor of an amino acid having pro-urolithiasis properties.

15. The method according to claim 14, wherein the precursor of the amino acid having pro-urolithiasis properties is selected from gamma-glutamylfelininylglycine (GG-FLN-GLY); and felininylglycine (FLN-GLY).

16. The method according to claim 12, wherein the effective amount of at least one of caprylic acid and capric acid is from about 1.1% to about 7% based on the total weight of the pet food composition.

17. The method according to claim 12, wherein the effective amount of at least one of DHA and EPA is from about 0.2% to about 3% by weight based on the total weight of the pet food composition.

18. The method according to claim 12, wherein the sulfur-containing amino acid is selected from: S-adenosylhomocysteine (SAH); cystathionine (CYST); glutathione disulfide (GSSG); cysteine-glutathione disulfide (CYSSG); or a combination of two or more thereof; and the sulfur-free byproduct is selected from: opthalmate (OPH); pyroglutamine (pGLN);

or a combination thereof.

* * * * *